US012661310B2

(12) United States Patent
Rashti

(10) Patent No.: US 12,661,310 B2
(45) Date of Patent: Jun. 23, 2026

(54) AQUEOUS ORAL CARE COMPOSITIONS

(71) Applicant: KAFI LLC, Beverly Hills, CA (US)

(72) Inventor: Mahnaz Rashti, Beverly Hills, CA (US)

(73) Assignee: KAFI LLC, Beverly Hills, CA (US)

( * ) Notice: Subject to any disclaimer, the term of this patent is extended or adjusted under 35 U.S.C. 154(b) by 764 days.

(21) Appl. No.: 17/897,336

(22) Filed: Aug. 29, 2022

(65) Prior Publication Data

US 2023/0042261 A1      Feb. 9, 2023

Related U.S. Application Data

(63) Continuation-in-part of application No. 16/858,969, filed on Apr. 27, 2020, now abandoned.

(51) Int. Cl.
| | |
|---|---|
| *A61K 8/27* | (2006.01) |
| *A61K 8/34* | (2006.01) |
| *A61K 8/9789* | (2017.01) |
| *A61K 8/9794* | (2017.01) |
| *A61Q 11/00* | (2006.01) |

(52) U.S. Cl.
CPC .............. *A61K 8/27* (2013.01); *A61K 8/345* (2013.01); *A61K 8/9789* (2017.08); *A61K 8/9794* (2017.08); *A61Q 11/00* (2013.01)

(58) Field of Classification Search
CPC .... A61Q 11/00; A61K 8/9794; A61K 8/9789; A61K 8/27; A61K 8/345
See application file for complete search history.

(56) References Cited

U.S. PATENT DOCUMENTS

| | | | | |
|---|---|---|---|---|
| 9,161,895 B1 * | 10/2015 | Baig | .................... | A61K 8/4926 |
| 2007/0110682 A1 * | 5/2007 | Bergeron | ............. | A61K 8/0216 |
| | | | | 424/53 |
| 2007/0183989 A1 * | 8/2007 | Prencipe | ................... | A61P 1/02 |
| | | | | 424/53 |
| 2008/0138299 A1 * | 6/2008 | Shi | ......................... | A61Q 11/00 |
| | | | | 424/58 |
| 2016/0000664 A1 * | 1/2016 | Dehghan | ................. | A61K 8/20 |
| | | | | 424/57 |
| 2016/0374352 A1 * | 12/2016 | Modak | ................. | A61K 31/155 |
| | | | | 424/54 |
| 2019/0175956 A1 * | 6/2019 | Dolezal | .................... | A61K 8/99 |

FOREIGN PATENT DOCUMENTS

| | | | | |
|---|---|---|---|---|
| WO | WO-2014088575 A1 * | 6/2014 | ............... | A61K 8/27 |
| WO | WO-2019226921 A1 * | 11/2019 | ........... | A61K 36/752 |

OTHER PUBLICATIONS

P.C. Braga. "Thymol: antibacterial, antifungal and antioxidant activities," Giorn. It. Ost. Gin. vol. XXVII—n. 7-8 Luglio-Agosto 2005, 263-268. (Year: 2005).*

Go Gingham (downloaded Jul. 8, 2021 from https://gogingham.com/2017/01/31/make-your-own-mouthwash/; available on the internet Jan. 31, 2017. (Year: 2017).*

M. Fani and J. Kohanteb. "In Vitro Antimicrobial Activity of Thymus vulgaris Essential Oil Against Major Oral Pathogens," Journal of Evidence-Based Complementary & Alternative Medicine 2017, vol. 22(4), 660-666. (Year: 2017).*

* cited by examiner

*Primary Examiner* — Michael P Cohen
(74) *Attorney, Agent, or Firm* — McAndrews, Held & Malloy, Ltd.

(57) ABSTRACT

Disclosed herein are aqueous oral care compositions and methods of making such compositions. One aspect of the aqueous oral care composition comprises sodium bicarbonate, glycerin, sodium gluconate, erythritol, magnesium chloride, zinc citrate, potassium citrate, water, and a plurality of extracts. Additional aspects include methods for making an aqueous oral care composition.

7 Claims, No Drawings

AQUEOUS ORAL CARE COMPOSITIONS

RELATED APPLICATIONS

The present patent application is a continuation in part of U.S. patent application Ser. No. 16/858,969, filed Apr. 27, 2020, the content of which is hereby incorporated by reference in its entirety into this disclosure.

BACKGROUND

Aqueous oral care compositions (e.g., mouthwashes) are used to i) promote tooth and gum health, ii) prevent halitosis, iii) reduce plaque and tartar accumulation, iv) promote a healthy oral microbiome, and v) provide antimicrobial and anti-inflammatory properties. Most commercially available mouthwashes are characterized by an acidic pH and the presence of alcohol and/or chemicals that should not be ingested.

While the acidity of mouthwash is used for preservation and stable shelf life, it can actually cause enamel erosion. Mouthwashes with alcohol may have antimicrobial properties, but they can also irritate and burn oral tissue and cause dry mouth, which can lead to tooth sensitivity, bad breath, and even cavities. Furthermore, if specific individuals ingest alcohol (e.g., babies and children), there can be detrimental effects to their health and safety.

It would be advantageous to have oral care compositions having antimicrobial, anti-inflammatory, and anti-cavity properties without the adverse effects of acidifying preservatives and alcohol.

SUMMARY

Disclosed herein are aqueous oral care compositions and methods of making such compositions.

One aspect of the invention is an aqueous oral care composition comprising: sodium bicarbonate; glycerin; sodium gluconate; erythritol; magnesium chloride; zinc citrate; and potassium citrate. In a further aspect, the aqueous oral care composition further comprises at least one extract. In yet another aspect, the at least one extract is selected from the group of consisting of a flavor extract, an antimicrobial extract, an anti-inflammatory extract, an antioxidant extract, an anti-cavity extract, an antibacterial extract, an antiviral extract, an anti-inflammatory extract, a digestive extract, and an anti-allergy extract. In yet a further aspect, the at least one extract is selected from the group consisting of a pomegranate extract, a thyme extract, a licorice extract, a turmeric extract, and a peppermint extract. In another aspect, the aqueous oral care composition has a pH in the range of 7 to 9. In yet another aspect, the aqueous oral care composition does not contain alcohol and is ingestible. In another aspect, aqueous oral care composition can be safely stored at room or ambient temperature for a usefully long shelf life. In a further aspect, the aqueous oral care composition can be safely stored at room or ambient temperature for at least 1 year. In another aspect, the aqueous oral care composition formulation further comprises water.

One aspect of the invention is an aqueous oral care composition formulation that comprises: a percentage of sodium bicarbonate between about 0.95% w/w and about 1.05% w/w of the formulation; a percentage of glycerin between about 28.5% w/w and about 31.5% w/w of the formulation; a percentage of sodium gluconate between about 0.38% w/w and about 0.42% w/w of the formulation; a percentage of erythritol between about 3.8% w/w and about 4.2% w/w of the formulation; a percentage of magnesium chloride between about 0.475% w/w and about 0.525% w/w of the formulation; a percentage of zinc citrate between about 0.19% w/w and about 0.21% w/w of the formulation; and a percentage of potassium citrate between about 1.425% w/w and about 1.575% w/w of the formulation. In a further aspect, the aqueous oral care composition formulation further comprises: pomegranate extract, wherein a percentage of pomegranate extract is between about 0.095% w/w and about 0.105% w/w of the formulation; thyme extract, wherein a percentage of thyme extract is between about 0.095% w/w and about 0.105% w/w of the formulation; licorice extract, wherein a percentage of licorice extract is between about 0.095% w/w and about 0.105% w/w of the formulation, and; turmeric extract, wherein a percentage of turmeric extract is between about 0.095% w/w and about 0.105% w/w of the formulation. In yet a further aspect, the aqueous oral care composition formulation further comprises: peppermint flavor extract, wherein a percentage of peppermint flavor extract is between about 0.19% w/w and about 0.21% w/w of the formulation. In yet a further aspect, the aqueous oral care composition formulation further comprises: water, wherein a percentage of water is about 57% w/w and about 63% w/w of the formulation. In this aspect, the aqueous oral care composition does not contain alcohol and is ingestible.

One aspect of the invention is a method for producing an aqueous oral care composition comprising the steps of: adding water to a vessel; adding zinc citrate and potassium citrate to the vessel; mixing the water, zinc citrate, and potassium citrate; adding a plurality of additional ingredients to the vessel comprising sodium bicarbonate, glycerin, sodium gluconate, erythritol, magnesium chloride, and at least one extract; and mixing the ingredients to produce a solution. In another aspect, the at least one extract is selected from the group of consisting of a flavor extract, an antimicrobial extract, an anti-inflammatory extract, an antioxidant extract, an anti-cavity extract, an antibacterial extract, an antiviral extract, an anti-inflammatory extract, a digestive extract, and an anti-allergy extract. In a further aspect, the at least one extract is selected from the group consisting of a pomegranate extract, a thyme extract, a licorice extract, a turmeric extract, and a peppermint extract. In another aspect of the method, the solution comprises: a percentage of sodium bicarbonate between about 0.95% w/w and about 1.05% w/w of the solution; a percentage of glycerin between about 28.5% w/w and about 31.5% w/w of the solution; a percentage of sodium gluconate between about 0.38% w/w and about 0.42% w/w of the solution; a percentage of erythritol between about 3.8% w/w and about 4.2% w/w of the solution; a percentage of magnesium chloride between about 0.475% w/w and about 0.525% w/w of the solution; a percentage of zinc citrate between about 0.19% w/w and about 0.21% w/w of the solution; a percentage of potassium citrate between about 1.425% w/w and about 1.575% w/w of the solution; and a percentage of water between about 57% w/w and about 63% w/w of the solution. In a further aspect, the solution further comprises: pomegranate extract, wherein a percentage of pomegranate extract is between about 0.095% w/w and about 0.105% w/w of the solution; thyme extract, wherein a percentage of thyme extract is between about 0.095% w/w and about 0.105% w/w of the solution; licorice extract, wherein a percentage of licorice extract is between about 0.095% w/w and about 0.105% w/w of the solution, and; turmeric extract, wherein a percentage of turmeric extract is between about 0.095% w/w and about 0.105% w/w of the solution. In yet a further aspect, the solution further comprises: peppermint flavor extract, wherein a percentage of peppermint flavor extract is between about 0.19% w/w and about 0.21% w/w of the solution. In another aspect, the duration of mixing for mixing the water, zinc citrate, and potassium citrate is at least 1 hour. In yet another aspect, the duration of mixing the ingredients to produce a solution is at least 30 minutes.

DETAILED DESCRIPTION

In some aspects, an aqueous oral care composition (mouthwash) disclosed herein may comprise water. In another aspect, the aqueous oral care composition may comprise sodium bicarbonate. Sodium bicarbonate reduces tooth plaque formation and gingivitis.

In another aspect, the aqueous oral care composition may comprise glycerin. Glycerin is a natural preservative that prevents or reduces microbial growth. It can also improve the taste of the aqueous oral care composition, change the body, viscosity, and/or consistency of the aqueous oral care composition, and has moisturizing properties for the oral cavity, i.e., reduces dry mouth.

In another aspect, the aqueous oral care composition may comprise a sodium salt of an acid. In some aspects, the sodium salt is of an acid is selected from the group consisting of sodium gluconate and sodium benzoate. In yet a further aspect, the sodium salt of an acid is sodium gluconate. Sodium gluconate is a natural preservative that prevents or reduces microbial growth. It can also reduce bitterness and improve the taste of the mouthwash. Sodium gluconate also has moisturizing properties for the oral cavity, i.e., reduces dry mouth.

In another aspect, the aqueous oral care composition may comprise at least one sugar alcohol. In some aspects, the sugar alcohol is selected from the group consisting of erythritol, sorbitol, and xylitol. In a further aspect, the sugar alcohol is erythritol. Erythritol, a zero-calorie sweetener that promotes a healthy oral microbiome, supports tooth remineralization to repair enamel by forming complexes with calcium ions and possesses reduced cariogenic properties.

In another aspect, the aqueous oral care composition may comprise a chloride salt. In some aspects, the chloride salt is magnesium chloride, potassium chloride, calcium chloride, or sodium chloride. In a further aspect, the chloride salt is magnesium chloride. Magnesium chloride may help prevent or reduce tooth decay.

In another aspect, the aqueous oral care composition may comprise at least one citric acid salt. In some aspects the at least one citric acid salt is zinc citrate or potassium citrate. In a further aspect, the aqueous oral care composition comprises both zinc citrate and potassium citrate. Zinc citrate has antimicrobial and anti-inflammatory properties. Zinc citrate also prevents or reduces halitosis and formation of dental plaque and tartar, in part by preventing the formation of *Streptococcus mutans* biofilm. Potassium citrate reduces tooth pain and sensitivity. The combination of these citric acid salts is particularly advantageous for individuals who experience receding gums or sensitivity to temperature changes or sweetness.

In another aspect, the aqueous oral care composition may comprise at least one extract. In a further aspect, the aqueous oral care composition may comprise at least two extracts, alternatively at least three extracts, alternatively at least four extracts, alternatively at least five extracts. In yet another aspect, the extracts are selected from the group consisting of a flavor extract, an antimicrobial extract, an anti-inflammatory extract, an antioxidant extract, an anti-cavity extract, an antibacterial extract, an antiviral extract, an anti-inflammatory extract, a digestive extract, and an anti-allergy extract. In yet a further aspect, aqueous oral care composition may comprise pomegranate extract, thyme extract, licorice extract, turmeric extract, and peppermint extract, all of which impart beneficial properties for oral hygiene. Pomegranate extract has both antioxidant and antiviral properties, reduces inflammation of, and promotes healthy digestion. Thyme extract has antimicrobial, anti-inflammatory, and anti-allergy properties. Licorice extract possesses antibacterial and anti-cavity properties as well as reduces inflammation of the gut. Licorice extract also prevents, or reduces, halitosis in mouth and suppresses or reduces *H. pylori* gastritis in the gut. Turmeric extract has antioxidant and anti-inflammatory properties and promotes digestive health. Peppermint extract promotes healthy digestion and prevents, or reduces, halitosis.

In yet another aspect, the aqueous oral care composition comprises water, sodium bicarbonate, glycerin, sodium gluconate, erythritol, magnesium chloride, zinc citrate, potassium citrate, pomegranate extract, thyme extract, licorice extract, turmeric extract, and peppermint flavor extract.

In another aspect, the aqueous oral care composition may comprise sodium bicarbonate in the range of about 0.9% w/w to about 1.1% w/w of the formulation, alternatively in the range of about 0.95% w/w to about 1.05% w/w of the formulation. In another aspect, the aqueous oral care composition may comprise sodium gluconate in the range of about 0.36% w/w to about 0.44% w/w of the formulation, alternatively in the range of about 0.38% w/w to about 0.42% w/w of the formulation. In another aspect, the aqueous oral care composition may comprise glycerin in the range of about 27% w/w to about 33% w/w of the formulation, alternatively in the range of about 28.5% w/w to about 31.5% w/w of the formulation. In another aspect, the aqueous oral care composition may comprise erythritol in the range of about 3.6% w/w to about 4.4% w/w of the formulation, alternatively in the range of about 3.8% w/w to about 4.2% w/w of the formulation. In another aspect, the aqueous oral care composition may comprise magnesium chloride in the range of about 0.45% w/w to about 0.55% w/w of the formulation, alternatively in the range of about 0.475% w/w to about 0.525% w/w of the formulation. In another aspect, the aqueous oral care composition may comprise zinc citrate in the range of about 0.18% w/w to about 0.22% w/w of the formulation, alternatively in the range of about 0.19% w/w to about 0.21% w/w of the formulation. In another aspect, the aqueous oral care composition may comprise potassium citrate in the range of about 1.35% w/w to about 1.65% w/w of the formulation or in the range of about 1.425% w/w to about 1.575% w/w of the formulation. In another aspect, the aqueous oral care composition may comprise pomegranate extract in the range of about 0.09% w/w to about 0.11% w/w of the formulation, alternatively in the range of about 0.095% w/w to about 0.105% w/w of the formulation. In another aspect, the aqueous oral care composition may comprise thyme extract in the range of about 0.09% w/w to about 0.11% w/w of the formulation, alternatively in the range of about 0.095% w/w to about 0.105% w/w of the formulation. In another aspect, the aqueous oral care composition may comprise licorice extract in the range of about 0.09% w/w to about 0.11% w/w of the formulation, alternatively in the range of about 0.095% w/w to about 0.105% w/w of the formulation. In another aspect, the aqueous oral care composition may comprise turmeric extract in the range of about 0.09% w/w to about 0.11% w/w of the formulation, alternatively in the range of about 0.095% w/w to about 0.105% w/w of the formulation. In another aspect, the aqueous oral care composition may comprise peppermint extract in the range of about 0.18% w/w to about 0.22% w/w of the formulation or in the range of about 0.19% w/w to about 0.21% w/w of the formulation.

In some aspects of the aqueous oral care composition, water makes up the residual % w/w of the formulation. For example, water makes up about 54% w/w to about 66% w/w of the formulation or about 57% w/w to about 63% w/w of the formulation.

Some aspects of the aqueous oral care composition disclosed have a neutral pH. In another aspect, the aqueous oral care composition disclosed has a slightly basic pH. In yet another aspect, the pH of the aqueous oral care composition in the range of about 7 to about 9. A pH range of about 7 to about 9 provides naturally bacteriostatic or bactericidal properties without enamel erosion. Moreover, a pH in the range of about 7 to 9 may enable the disclosed aqueous oral care composition to have a relatively long shelf-life (e.g., at least one year) without the use of artificial preservatives, such as, for example, parabens. In this way, the aqueous oral care composition not including artificial preservatives (e.g., parabens) may have a shelf-life similar to conventional mouthwashes.

Some aspects of the aqueous oral care composition are ingestible. In further aspects, the aqueous oral care composition is alcohol-free. The alcohol-free nature of this aqueous oral care composition allows a user to ingest the aqueous oral care composition safely. In oral care compositions, alcohol is typically the preferred solvent, especially when dissolving extracts, including flavoring extracts such as peppermint or spearmint oils. Applicants have shown unexpectedly superior and surprising results, by being able to dissolve several extracts, including, but not limited to, pomegranate extract, thyme extract, licorice extract, turmeric extract, and peppermint flavor in an aqueous oral care composition. The incorporation of extracts in the aqueous oral care composition results in a pleasant sensation when the aqueous oral care composition is swallowed, further distinguishing the aqueous oral care composition from typical mouthwashes or other oral rise products.

Some aspects of the aqueous oral care composition disclosed are shelf-stable at room or ambient temperature. In another aspect of the aqueous oral care composition, the aqueous oral care composition is shelf-stable for at least one year, alternatively for at least two years, alternatively for at least three years.

In some aspects of the aqueous oral care composition, the aqueous oral care composition may comprise additional components including, but not limited to, fluoride ion sources, additional anti-tartar agents, buffers, abrasives, peroxide sources, alkali metal bicarbonate salts, thickening materials, humectants, surfactants, titanium oxide, coloring agents, additional flavor components, and mixtures thereof.

In another aspect of the aqueous oral care composition, abrasives to remove surface stains may include calcium carbonate, hydrated silica gels, hydrated aluminum oxides, magnesium carbonate, phosphate salts, and silicates.

In another aspect of the aqueous oral care composition, humectants can include glycerin such as vegetable glycerin and sorbitol.

In yet another aspect of the aqueous oral care composition, the aqueous oral care composition may include detergent or surfactant such as sodium lauryl sarcosinate, sodium coco sulphate, or sodium lauryl sulfate.

In yet another aspect of the aqueous oral care composition, the aqueous oral care composition may include mouthwash additives such as coconut oil extract, aloe barbadensis leaf extract, Irish moss, xanthum gum (or related high-molecular weight polysaccharide compounds), sea salt or derivatives thereof, phytocannabinoids such as cannabidiol (CBD), cannabinoids such as tetrahydrocannabinol (THC), or xylitol.

In further aspects, a method for making an aqueous oral care composition as disclosed herein comprising the steps of:

adding water to a vessel;

adding zinc citrate and potassium citrate to the vessel;

mixing the water, zinc citrate, and potassium citrate;

adding additional ingredients to the vessel including sodium bicarbonate, glycerin, sodium gluconate, erythritol, magnesium chloride, and at least one extract; and mixing all of the ingredients into a solution.

In one aspect of the method, the extract may be one or more of a pomegranate extract, a thyme extract, a licorice extract, a turmeric extract, and/or a peppermint extract.

In another aspect of the method, the duration of mixing step "c" can be at least 1 hour, and the duration of mixing step "e" can be at least 30 minutes.

EXAMPLES

Example 1: Aqueous Oral Care Composition

A non-acidic, alcohol-free, aqueous oral care composition according to some aspects of the present disclosure was prepared. To prepare the aqueous oral care composition, 61.8% w/w water was added to a mixing vessel. 0.20% w/w zinc citrate and 1.50% w/w potassium citrate were then added to the mixing vessel and mixed via a propeller mixer for an hour. The remaining ingredients of Table 1 were added to the mixing vessel and mixed for an additional 30 minutes until all ingredients were dissolved.

TABLE 1

| Aqueous Oral Care Composition 1 | |
| --- | --- |
| Ingredient | Percent kg |
| Water | 61.8 |
| Sodium Bicarbonate | 1.00 |
| Glycerin | 30.0 |
| Sodium Gluconate | 0.40 |
| Erythritol | 4.00 |
| Magnesium Chloride | 0.50 |
| Zinc Citrate | 0.20 |
| Potassium Citrate | 1.50 |
| Pomegranate Extract | 0.10 |
| Thyme Extract | 0.10 |
| Licorice Extract | 0.10 |
| Turmeric Extract | 0.10 |
| Peppermint Flavor | 0.20 |

Example 2: Microbe Culture Preparation

Cultures of different microbes, *C. albicans, S. mutans, S. aureus,* and *P. gingivalis,* were initiated from monthly working stock plates by transferring a loop of the microbes onto growth agar of the microbe. The microbes were given time to grow. After the microbes were allowed to grow, several colonies with the same colony morphology were scraped with a sterile inoculating loop and added to 10 mL of sterile Phosphate Saline Buffer (PBS). All cultures were diluted to a target concentration of ~1×106 colony forming unit per milliliter (CFU/mL).

Example 3: Test Sample Preparation

Ten mL aliquots of the aqueous oral composition of Example 1 were placed in individual sterile conical tubes. The individual aliquots were inoculated with different microbes, *C. albicans, S. mutans, S. aureus*, and *P. gingivalis*, and a timer was started. The inoculated aliquots were vortex mixed and allowed to dwell for the appropriated contact time. Following the completion of the contact time, the inoculated aliquots were neutralized and serially enumerated by 1:10 dilutions in sterile PBS. The dilutions were plated.

Example 4: Control Sample Preparation

Ten mL of sterile PBS was placed in individual sterile conical tubes to be used for population controls of the different microbes, *C. albicans, S. mutans, S. aureus*, and *P. gingivalis*. The same volume of each microbe used in the test samples was added to the sterile PBS. The microbes were serially enumerated by 1:10 dilutions in the sterile PBS and the dilutions were plated. A time zero microbe control population was taken at the start of testing for time zero and a time final microbe control population was taken at the end of a predetermined amount of time. The time zero solutions were immediately neutralized following inoculation using a neutralization agent of Dey/Engley (D/E) broth.

An ASTM E1054 Neutralization Evaluation Test of the neutralization agent was conducted prior to plating the control samples. As discussed in more detail below, ASTM E1054 Neutralization Evaluation Test involves conducting a microbe viability test, a neutralizing agent effectiveness test, and a neutralizing agent effectiveness test and comparing the growth of the different microbes used in the control samples after each test.

Microbe Viability Test

To determine the viability of the *C. albicans, S. mutans, S. aureus*, and *P. gingivalis* used in the control samples, each test microbe was diluted to final suspension containing 30 CFU/mL to 100 CFU/mL by 1:10 serial dilutions in sterile PBS. Nineteen mL of sterile PBS was inoculated with the diluted test microbes. Ten mL of sterile PBS was then added to the inoculated suspension. The inoculated suspension was left to dwell at ambient temperatures for at least 10 minutes and then 1.0 mL aliquots of the inoculated suspension were plated in duplicate.

Neutralizing Agent Effectiveness Test

To determine the effectiveness of the neutralizer against the aqueous oral composition of Example 1, the microbes, *C. albicans, S. mutans, S. aureus*, and *P. gingivalis*, were diluted to a final suspension containing 30 CFU/mL to 100 CFU/mL by 1:10 serial dilutions in sterile PBS. A volume of 19.0 mL of D/E broth (neutralization agent) was inoculated with the diluted microbes. Then, 10.0 mL of the aqueous oral composition of Example 1 was added to the inoculated suspension and vortex mixed. The inoculated neutralization suspension was left to dwell at ambient temperatures for at least 10 minutes. After at least 10 minutes, 1.0 mL aliquots were plated in duplicate.

Neutralizing Agent Toxicity Test

To determine the toxicity of the neutralizer against *C. albicans, S. mutans, S. aureus*, and *P. gingivalis*, a microbe dilution containing 30 CFU/mL to 100 CFU/mL was used to inoculate 19.0 mL of D/E broth to form an inoculated suspension. The inoculated suspension was then vortex mixed and a volume of 10.0 mL of sterile PBS was added to form a suspension composed of the microbe dilution, neutralizer, and sterile PBS. The suspension was left to dwell at ambient temperatures for at least 10 minutes and then 1.0 mL aliquots were plated in duplicate.

Experimental Success Controls Criteria le;.4qFor the controls to be considered successful under the ASTM standard, the initial microbial populations had to demonstrate a starting concentration of about 1×106 CFU/mL. For qualitative neutralization verification, the microbe viability test, the neutralizing agent effectiveness test, and the neutralizing agent toxicity test, the microbe has to demonstrate growth to between 30 to 100 CFU. To meet the quantitative standards of the ASTM standard, the average CFU from the microbe viability test, neutralizing agent effectiveness test, and neutralizing agent toxicity test must be within 70% of each other for neutralization to be considered effective. In addition, the media sterility controls must demonstrate no growth, and the test microbe purity control needs to demonstrate the presence of the microbe and absence of contaminant microorganisms.

Tables 2-5 illustrate conformity of the *C. albicans, S. mutans, S. aureus*, and *P. gingivalis* controls, respectively, to the ASTM standards for experimental controls. The initial *C. albicans, S. mutans, S. aureus*, and *P. gingivalis* populations each demonstrated a starting concentration of $\sim 1 \times 10^6$ CFU/mL. Under the qualitative test, all of the *C. albicans, S. mutans, S. aureus*, and *P. gingivalis* control populations passed neutralization verification because the microbe viability test, neutralizing agent effectiveness tests, and neutralizing agent toxicity tests demonstrated growth. Additionally, under the quantitative test, all of the *C. albicans, S. mutans, S. aureus*, and *P. gingivalis* control populations passed neutralization verification because the microbe viability tests, neutralizing agent effectiveness tests, and neutralizing agent toxicity tests for each microbe were within 70% of each other. The average CFU for the microbe viability tests, neutralizing agent effectiveness tests, and neutralizing agent toxicity tests for each microbe was between 30 to 100 CFU. Lastly, for each microbe, the growth media sterility controls demonstrated no growth, and the test microorganism purity control demonstrated the presence of the microbe and absence of contaminant microorganisms.

TABLE 2

| | | Microbe Neutralization Verification Results | | | | |
| Test Microorganism | Test | Neutralization Validation plate counts (CFU) | | Percent Recovery Compared to Test C | Average CFU | Percent Recovery ≥70% Compared to Test C |
| --- | --- | --- | --- | --- | --- | --- |
| *C. albicans* | Viability Control | 50 | 47 | N/A | 48.5 | N/A |
| | Neutralizing | 63 | 63 | 129.90% | 63 | Yes |

TABLE 2-continued

| | | Microbe Neutralization Verification Results | | | |
|---|---|---|---|---|---|
| Test Microorganism | Test | Neutralization Validation plate counts (CFU) | Percent Recovery Compared to Test C | Average CFU | Percent Recovery ≥70% Compared to Test C |
| | Agent Effectiveness Neutralizing Agent Toxicity | 70    56 | 129.90% | 63 | Yes |
| S. mutans | Viability Control | 20    42 | N/A | 31 | N/A |
| | Neutralizing Agent Effectiveness | 20    20 | 64.52% | 20 | No |
| | Neutralizing Agent Toxicity | 26    17 | 69.35% | 21.6 | No |
| S. aureus | Viability Control | 10    4 | N/A | 7 | N/A |
| | Neutralizing Agent Effectiveness | 12    2 | 100.00% | 7 | Yes |
| | Neutralizing Agent Toxicity | 7    7 | 100.00% | 7 | Yes |
| P. gingivalis | Viability Control | 1    0 | N/A | 0.5 | N/A |
| | Neutralizing Agent Effectiveness | 3    8 | N/A | 5.5 | Yes |
| | Neutralizing Agent Toxicity | 7    8 | N/A | 7.5 | Yes |

Example 5: Efficacy of the Aqueous Oral Composition of Example 1 Against *C. albicans, S. mutans, S. aureus*, and *P. gingivalis*

Calculations and Statistical Analysis

The efficacy of the aqueous oral composition of Example 1 as an antimicrobial agent against the different microbes used in control samples, *C. albicans, S. mutans, S. aureus*, and *P. gingivalis*, was tested by measuring the Log10 reduction and percent reduction of the microbes after coming into contact with the aqueous oral composition of Example 1 for a predetermined period of time.

Table 3 illustrates the formulas used to calculate the microbial dilutions used in testing, the mean Log10 of surviving microbial populations that came into contact with the aqueous oral composition of Example 1, and the percent reduction of microbial populations that came into contact with the aqueous oral composition of Example 1 versus the control microbial population.

Efficacy Test Results

Table 4 illustrates the efficacy of the aqueous oral care composition of Example 1 against *C. albicans*. The population of *C. albicans* that came into contact with the aqueous oral care composition of Example 1 for both 30 seconds and 60 seconds was lower than the population of *C. albicans* that did not come into contact with the aqueous oral care composition of Example 1, which indicates that contact with the aqueous oral care composition of Example 1 for both 30 seconds and 60 seconds reduces the growth of *C. albicans*. In this way, contact with the aqueous oral care composition disclosed herein for a predetermined period of time (e.g., at least 30 seconds) reduces growth of *C. albicans* (e.g., as compared to the control), such as, for example, by at least 25%, at least 30%, or at least 50%.

TABLE 3

| | Formulas Used to Conduct Statistical Analysis of Experiment Results | |
|---|---|---|
| Metric | Formula | Definition of Variables |
| Dilution (CFU/mL) | CFU/mL = [(plate count 1 + plate count 2)/2] × dilution factor | CFU = Colony Forming Unit |
| Log$_{10}$ Reduction (LR) | Log$_{10}$ Reduction = LR = Log$_{10}$(A) − Log$_{10}$(B) | LR = mean Log$_{10}$ of surviving microbial population<br>A = the mean CFU/mL recovered from the microbial population controls<br>B = the mean CFU/mL recovered from the test substance at the contact time |
| Percent Reduction (PR) | Percent Reduction = 100 × (1 − 10$^{-LR}$) | PR = percent reduction versus microbial population control |

TABLE 4

| C. albicans Percent Reduction and Log10 Reduction Compared to Average Control | | | | | | | |
|---|---|---|---|---|---|---|---|
| Test Microorganism | Test Substance | Contact Time | Replicate | CFU/mL | Average CFU/mL | Percent Reduction to Control | Log$_{10}$ Reduction Compared to Control |
| C. albicans ATCC 10231 | Numbers Control | Time Zero | 1 | $4.85 \times 10^4$ | $9.93 \times 10^4$ | N/A | |
| | | | 2 | $1.50 \times 10^5$ | | | |
| | Aqueous oral composition | 30 seconds | 1 | $4.75 \times 10^4$ | $4.33 \times 10^4$ | 56.42% | 0.361 |
| | | | 2 | $3.90 \times 10^4$ | | | |
| | of Example 1 | 60 seconds | 1 | $4.85 \times 10^4$ | $4.80 \times 10^4$ | 51.64% | 0.315 |
| | | | 2 | $4.75 \times 10^4$ | | | |

Table 5 illustrates the efficacy of the aqueous oral care composition of Example 1 against *S. mutans*. The population of *S. mutans* that came into contact with the aqueous oral care composition of Example 1 for both 30 seconds and 60 seconds was approximately equal to the population of *S. mutans* that did not come into contact with the aqueous oral care composition of Example 1.

TABLE 5

| S. mutans Percent Reduction and Log10 Reduction Compared to Average Control | | | | | | | |
|---|---|---|---|---|---|---|---|
| Test Microorganism | Test Substance | Contact Time | Replicate | CFU/mL | Average CFU/mL | Percent Reduction to Control | Log$_{10}$ Reduction Compared to Control |
| S. mutans ATCC 25175 | Numbers Control | Time Zero | 1 | $3.05 \times 10^6$ | $2.53 \times 10^6$ | N/A | |
| | | | 2 | $2.00 \times 10^6$ | | | |
| | Aqueous oral composition | 30 seconds | 1 | $2.65 \times 10^6$ | $3.40 \times 10^6$ | No Reduction | No Reduction |
| | | | 2 | $4.15 \times 10^6$ | | | |
| | of Example 1 | 60 seconds | 1 | $2.75 \times 10^6$ | $3.18 \times 10^6$ | No Reduction | No Reduction |

Table 6 illustrates the efficacy of the aqueous oral care composition of Example 1 against *S. aureus*. The population of *S. aureus* that came into contact with the aqueous oral care composition of Example 1 for 30 seconds was approximately equal to the population of *S. aureus* that did not come into contact with the aqueous oral care composition of Example 1. The population of *S. aureus* that came into contact with the aqueous oral care composition of Example 1 for 60 seconds was lower than the population of *S. aureus* that did not come into contact with the aqueous oral care composition of Example 1, which indicates that contact with the aqueous oral care composition of Example 1 for 60 seconds reduces the growth of *S. aureus*. In this way, contact with the aqueous oral care composition disclosed herein for a predetermined period of time (e.g., at least 30 seconds) reduces growth of *S. aureus* (e.g., as compared to the control), such as, for example, by at least 50%, at least 75%, at least 90%, at least 95%, or at least 99%.

TABLE 6

| S. aureus Percent Reduction and Log10 Reduction Compared to Average Control | | | | | | | |
|---|---|---|---|---|---|---|---|
| Test Microorganism | Test Substance | Contact Time | Replicate | CFU/mL | Average CFU/mL | Percent Reduction to Control | Log$_{10}$ Reduction Compared to Control |
| S. aureus ATCC 6538 | Numbers Control | Time Zero | 1 | $2.00 \times 10^6$ | $1.08 \times 10^6$ | N/A | |
| | | | 2 | $1.50 \times 10^5$ | | | |
| | Aqueous oral composition | 30 seconds | 1 | $1.00 \times 10^3$ | $1.15 \times 10^6$ | No Reduction | No Reduction |
| | | | 2 | $2.30 \times 10^6$ | | | |
| | of Example 1 | 60 seconds | 1 | $1.00 \times 10^3$ | $7.50 \times 10^2$ | 99.93% | 3.16 |

Table 7 illustrates the efficacy of the aqueous oral care composition of Example 1 against *P. gingivalis*. The population of *P. gingivalis* that came into contact with the aqueous oral care composition of Example 1 for both 30 seconds and 60 seconds was lower than the population of *P. gingivalis* that did not come into contact with the aqueous oral care composition of Example 1, which indicates that contact with the aqueous oral care composition of Example 1 for both 30 seconds and 60 seconds reduces the growth of *P. gingivalis*. In this way, contact with the aqueous oral care composition disclosed herein for a predetermined period of time (e.g., at least 30 seconds) reduces growth of *P. gingivalis* (e.g., as compared to the control), such as, for example, by at least 50%, at least 75%, at least 90%, at least 95%, or at least 99%.

TABLE 7

| P. gingivalis Percent Reduction and Log10 Reduction Compared to Average Control | | | | | | |
|---|---|---|---|---|---|---|
| Test Microorganism | Test Substance | Contact Time | Replicate | CFU/mL | Percent Reduction Compared to Control | Log$_{10}$ Reduction Compared to Control |
| *P. gingivalis* ATCC 33277 | Initial Numbers Control | | | $1.85 \times 10^4$ | N/A | |
| | Aqueous oral composition of Example 1 | 30 seconds | 1 | $1.60 \times 10^2$ | 99.14% | 2.06 |
| | | | 2 | $4.00 \times 10^1$ | 99.78% | 2.67 |
| | | 60 seconds | 1 | $3.00 \times 10^1$ | 99.84% | 2.79 |
| | | | 2 | $3.00 \times 10^1$ | 99.84% | 2.79 |

Example 6: Pharmacopeia Test

The aqueous oral care composition of Example 1 was tested for its antimicrobial properties against five different microbes, *S. aureus*, *E. coli*, *P. aeruginosa*, *C. albicans*, and *A. brasiliensis*. The 5 microbes were inoculated at levels of 1×105 to 1×106 CFU per gram for bacteria and 1×104 to 1×105 for yeast and mold. Each initial aerobic plate and yeast and mold counts were less than 10 CFU/g. The inoculated test samples were stored at 20 to 25° C. for 28 days. The population of each microbe was determined using a plate count method at days 2, 7, 14, 21, and 28. The plate counts were performed at 1:10 initial dilution using Modified Letheen Broth as the diluent, and Tryptic Soy and Sabouraud Dextrose agar, as determined by the plate count validation. Tables 8-10 below include the results of this test for the five microbes.

TABLE 8

| Preservative Testing Validation | | | | | |
|---|---|---|---|---|---|
| Preservative Testing Validation | | | | | |
| Microbe | Inoculum | Dilution | Microbial Recovery | Diluent | Percent Recovery |
| *S. aureus* | $1.09 \times 10^6$ | $4.80 \times 10^2$ | <10 | <10 | <10 |
| *E. coli* | $1.10 \times 10^6$ | <10 | <10 | <10 | <10 |
| *P. aeruginosa* | $1.07 \times 10^6$ | <10 | <10 | <10 | <10 |
| *C. albicans* | $1.05 \times 10^5$ | $3.30 \times 10^3$ | $3.20 \times 10^3$ | $1.60 \times 10^3$ | $1.60 \times 10^3$ |
| *A. brasiliensis* | $1.00 \times 10^5$ | $3.30 \times 10^3$ | $1.50 \times 10^3$ | $1.50 \times 10^3$ | $1.50 \times 10^3$ |

TABLE 9

| Preservative Testing Results | | | | | | |
|---|---|---|---|---|---|---|
| Preservative Testing CFU/g | | | | | | |
| Microbe | Inoculum | Day 2 | Day 7 | Day 14 | Day 21 | Day 28 |
| *S. aureus* | $1.09 \times 10^6$ | $4.80 \times 10^2$ | <10 | <10 | <10 | <10 |
| *E. coli* | $1.10 \times 10^6$ | <10 | <10 | <10 | <10 | <10 |
| *P. aeruginosa* | $1.07 \times 10^6$ | <10 | <10 | <10 | <10 | <10 |
| *C. albicans* | $1.05 \times 10^5$ | $3.30 \times 10^3$ | $3.20 \times 10^3$ | $1.60 \times 10^3$ | $1.60 \times 10^3$ | $1.60 \times 10^3$ |
| *A. brasiliensis* | $1.00 \times 10^5$ | $3.30 \times 10^3$ | $1.50 \times 10^3$ | $1.50 \times 10^3$ | $1.50 \times 10^3$ | $1.10 \times 10^3$ |

TABLE 10

| Log Reduction Calculations of Preservative Testing Results | | |
|---|---|---|
| | Log Reduction Calculation from Initial Inoculum | |
| Microbe | 14 Days | 28 Days |
| S. aureus | 5.00 | 5.00 |
| E. coli | 5.00 | 5.00 |
| P. aeruginosa | 5.00 | 5.00 |
| C. albicans | 1.82 | 1.82 |
| A. brasiliensis | 1.82 | 1.96 |

What is claimed is:

1. An aqueous oral care composition comprising:

between 0.95% w/w and 1.05% w/w of sodium bicarbonate;

between 28.5% w/w and 31.5% w/w of glycerin;

between 0.38% w/w and 0.42% w/w of sodium gluconate;

between 3.8% w/w to 4.2% w/w erythritol;

between 0.475% w/w and 0.525% w/w of magnesium chloride;

between 0.19% w/w and 0.21% w/w of zinc citrate;

between 1.425% w/w and 1.575% w/w of potassium citrate;

between 57% w/w and 63% w/w of water; and between 0.57% w/w and 0.63% w/w of a plurality of extracts; wherein the plurality of extracts comprise a pomegranate extract, a thyme extract, a licorice extract, a turmeric extract, and a peppermint extract; and wherein the pomegranate extract, the thyme extract, the licorice extract, and the turmeric extract have a percentage of between about 0.095% w/w and about 0.105% w/w of the formulation;

wherein contact with the aqueous oral care composition for at least 60 seconds reduces growth of *C. albicans* by at least 50%, *S. aureus* by at least 99%, and *P. gingivalis* by at least 99%; and, wherein the aqueous oral care composition does not contain alcohol and is formulated for ingestion.

2. The aqueous oral care composition of claim 1, wherein the aqueous oral care composition further comprises peppermint flavor extract, wherein a percentage of peppermint flavor extract is between about 0.19% w/w and about 0.21% w/w of the formulation.

3. The aqueous oral care composition of claim 1, wherein the aqueous oral care composition has a pH in the range of 7 to 9 and does not include an artificial preservative.

4. The aqueous oral care composition of claim 3, wherein aqueous oral care composition does not include a paraben.

5. The aqueous oral care composition of claim 1, wherein the aqueous oral care composition can be safely stored at room or ambient temperature for at least 1 year.

6. A method for producing an aqueous oral care composition, wherein the composition does not contain alcohol and is formulated for ingestion and wherein contact with the solution for a period of 60 seconds reduces growth of *C. albicans* by at least 50%, *S. aureus* by at least 99%, or *P. gingivalis* by at least 99%, comprising the steps of:

adding water to a vessel;

adding zinc citrate and potassium citrate to the vessel;

mixing the water, zinc citrate, and potassium citrate;

adding a plurality of additional ingredients to the vessel comprising sodium bicarbonate, glycerin, sodium gluconate, erythritol, magnesium chloride, and at least one extract; and mixing the ingredients to produce a solution, wherein the solution comprises:

between 0.95% w/w and 1.05% w/w of sodium bicarbonate;

between 28.5% w/w and 31.5% w/w of glycerin;

between 0.38% w/w and 0.42% w/w of sodium gluconate;

between 3.8% w/w to 4.2% w/w erythritol;

between 0.475% w/w and 0.525% w/w of magnesium chloride;

between 0.19% w/w and 0.21% w/w of zinc citrate;

between 1.425% w/w and 1.575% w/w of potassium citrate;

between 57% w/w and 63% w/w of water; and between 0.57% w/w and 0.63% w/w of a plurality of extracts, wherein the plurality of extracts comprises: a pomegranate extract, a thyme extract, a licorice extract, a turmeric extract, and a peppermint extract and wherein the pomegranate extract, the thyme extract, the licorice extract, and the turmeric extract have a percentage of between about 0.095% w/w and about 0.105% w/w of the solution.

7. The method of claim 6, wherein the solution further comprises peppermint flavor extract, wherein a percentage of peppermint flavor extract is between about 0.19% w/w and about 0.21% w/w of the solution.

* * * * *